(12) United States Patent
Keitel et al.

(10) Patent No.: US 10,233,417 B2
(45) Date of Patent: Mar. 19, 2019

(54) CONTAINER WITH FLEXIBLE WALLS

(71) Applicant: Sartorius Stedim Biotech GmbH, Goettingen (DE)

(72) Inventors: Heinz-Ruediger Keitel, Melsungen (DE); Bernward Husemann, Goettingen (DE); Wolfgang Kahlert, Koerle (DE)

(73) Assignee: Sartorius Stedim Biotech GmbH (DE)

( * ) Notice: Subject to any disclaimer, the term of this patent is extended or adjusted under 35 U.S.C. 154(b) by 291 days.

(21) Appl. No.: 14/917,726

(22) PCT Filed: Aug. 21, 2014

(86) PCT No.: PCT/EP2014/067856
§ 371 (c)(1),
(2) Date: Mar. 9, 2016

(87) PCT Pub. No.: WO2015/032629
PCT Pub. Date: Mar. 12, 2015

(65) Prior Publication Data
US 2016/0215248 A1    Jul. 28, 2016

(30) Foreign Application Priority Data

Sep. 9, 2013   (DE) .................. 10 2013 109 820

(51) Int. Cl.
*C12M 1/00*   (2006.01)
*C12M 1/21*   (2006.01)
(Continued)

(52) U.S. Cl.
CPC ............ *C12M 23/26* (2013.01); *C12M 23/14* (2013.01); *C12M 23/28* (2013.01); *C12M 23/34* (2013.01);
(Continued)

(58) Field of Classification Search
CPC ...... C12M 23/14; C12M 23/26; C12M 23/28; C12M 23/34; C12M 41/02; C12M 41/44; C12M 41/48
See application file for complete search history.

(56) References Cited

U.S. PATENT DOCUMENTS

| 5,922,112 | A | 7/1999 | Zappi et al. | |
| 7,088,932 | B2 * | 8/2006 | Chou et al. | ............... G03G 9/12 |
| | | | | 399/57 |

(Continued)

FOREIGN PATENT DOCUMENTS

| CN | 101163915 A | 4/2008 |
| CN | 102892487 A | 1/2013 |

(Continued)

OTHER PUBLICATIONS

International Preliminary Report on Patentability dated March 15, 2016.

(Continued)

*Primary Examiner* — Gautam Prakash
(74) *Attorney, Agent, or Firm* — Gerald E. Hespos; Michael J. Porco; Matthew T. Hespos

(57) ABSTRACT

A container (2) has flexible walls surrounding a container interior (6). At least one electrical sensor (3, 3', 3", 3''', 3'''') projects into the container interior (6) and has at least first and second electrically conductive plates (8, 8', 9, 9', 9''') for determining the conductivity or impedance of a medium that surrounds the plates (8, 8', 9, 9', 9'''). The plates (8, 8', 9, 9', 9''') are connected via connecting lines (10, 11) to a control and regulating unit (4) outside the container interior (6). At least the first plate (8, 8') is on a closed free end of a sheathing (5, 5', 5'''') and has a contact area exposed to the surrounding medium. The sheathing (5, 5', 5'''', 17, 17'''') is a flexible hose (7) or bellows (19, 19'''') through which the
(Continued)

electrical connecting line (10, 11) of the plate (8, 8', 9, 9', 9''') is routed.

13 Claims, 5 Drawing Sheets

(51) Int. Cl.
    *C12M 1/34*     (2006.01)
    *C12M 1/36*     (2006.01)

(52) U.S. Cl.
    CPC ............ *C12M 41/02* (2013.01); *C12M 41/44* (2013.01); *C12M 41/48* (2013.01)

(56) References Cited

U.S. PATENT DOCUMENTS

| | | |
|---|---|---|
| 7,879,599 B2 | 2/2011 | Goodwin |
| 8,124,403 B2 | 2/2012 | Goodwin |
| 8,678,638 B2 | 3/2014 | Wong |
| 2006/0240546 A1 | 10/2006 | Goodwin |
| 2007/0185472 A1 | 8/2007 | Baumfalk et al. |
| 2009/0147617 A1 | 6/2009 | Baumfalk et al. |
| 2011/0097789 A1 | 4/2011 | Goodwin |
| 2011/0187388 A1 | 8/2011 | Ossart |
| 2011/0249526 A1 | 10/2011 | Wong |
| 2012/0097557 A1 | 4/2012 | Baumfalk et al. |
| 2013/0039810 A1 | 2/2013 | Riechers |
| 2013/0101982 A1 | 4/2013 | Goodwin et al. |
| 2013/0170315 A1 | 7/2013 | Martens |
| 2014/0293734 A1 | 10/2014 | Kauling et al. |

FOREIGN PATENT DOCUMENTS

| | | |
|---|---|---|
| DE | 41 42 967 | 7/1993 |
| DE | 10 2010 007 559 | 8/2011 |
| EP | 1102047 A1 | 5/2001 |
| EP | 2 381 249 | 10/2011 |
| WO | 2009/093995 | 7/2009 |
| WO | 2011/082787 | 7/2011 |
| WO | 2011082787 A1 | 7/2011 |
| WO | 2011/112680 | 9/2011 |

OTHER PUBLICATIONS

International Search Report.
Chinese Search Report dated August 21, 2014.

\* cited by examiner

CONTAINER WITH FLEXIBLE WALLS

BACKGROUND

1. Field of the Invention

The invention relates to a container with flexible walls that surround a container interior. At least one electrical sensor projects into the container interior and has at least two electrically conductive plates. The conductivity or impedance of a medium that surrounds the plates can be determined. The plates are connected via connecting lines to a control and regulating unit arranged outside the container interior.

2. Description of the Related Art

US 2011/0187388 A1 discloses a bioreactor with a container with flexible walls that surround a container interior and at least one electrical sensor projecting into the container interior. In this case, electrically conductive plates or electrodes can be used to determine the conductivity or impedance of a medium that surrounds the plates. The plates are connected via connecting lines to a control and regulating unit arranged outside the container interior.

It is disadvantageous in this regard that the sensors or their electrode surfaces are arranged directly on the wall. Although this enables the container, including the sensors, to be folded up, it has the disadvantage that the one or more sensors cannot be adjusted to differing fill levels.

US 2011/0187388 A1 also discloses a container with rigid walls having a sensor arranged within the container interior on the free end of a rigid cylindrical sheathing that is mounted so as to be displaceable within an adapter that penetrates the top wall.

It is disadvantageous in this regard that leaks and contamination may arise between the displaceable sheathing and the adapter. In particular, contamination results if the sheathing is displaced from the exterior into the interior. If the cylindrical sheathing is not connected to the adapter in a displaceable manner, the height of the sensor cannot be adjusted, making it impossible to adjust to differing fill levels. Furthermore, it is also impossible to fold up flat a bioreactor with a container having flexible walls and a sensor arranged in a rigid cylindrical sheathing whose position relative to the fill level remains fixed.

DE 41 42 967 A1 discloses a bioreactor whose container has rigid walls and a top through which a cylindrical measurement probe is introduced from the exterior up to the maximum fill level of the bioreactor in order to eliminate foam. This probe is used to detect foam forming on the surface of the fermentation broth and measure its height. The measurement signal from the probe is fed into a regulating unit arranged outside the container. Depending on the height of the foam above the fermentation broth, a pump installed in an inlet line is actuated and causes an antifoam agent to be fed into the bioreactor from a container.

It is also disadvantageous with regard to this known bioreactor that problems with sealing and contamination between the probe and top or the container interior can occur with a displaceable probe. To the extent the probe is permanently connected to the top, it is no longer possible to adjust the fill level. If different fill levels are to be covered with a fixed probe arrangement using such a probe, the probe is relatively complicated and cost-intensive in structure.

U.S. Pat. No. 5,922,112 A discloses a bioreactor for wastewater that is open on top and has an electrical sensor for foam measurement that projects from above into the container interior. The sensor is connected via a control and regulating unit to a pump arranged in a line between a container containing antifoam agent and the bioreactor.

Furthermore, DE 10 2010 007 559 A1 discloses a bioreactor with a container with flexible walls that has an optical sensor for foam measurement that can be laterally arranged from the exterior. This optical sensor, which has essentially proven its usefulness, is reusable as it does not come into contact with the container interior, the fluid contained therein or any potential foam layer, and because it is separated from the container interior by a transparent window arranged in the container wall. Such an optical sensor is relatively cost-intensive, particularly if it is able to detect differing fill levels.

The present invention seeks to solve the problem of providing a bioreactor having a container with flexible walls and at least one low-cost electrical sensor for measuring the conductivity or impedance of a medium arranged in the container. The container with the sensor should be suitable for single use and be capable of being folded up to a small volume when empty.

SUMMARY

This problem is solved by a container with flexible walls that surround a container interior. At least one electrical sensor projects into the container interior and has electrically conductive plates that can determine the conductivity or impedance of a medium that surrounds the plates. Connecting lines connect the plates to a control and regulating unit arranged outside the container interior. At least one first plate is arranged on a closed, free end of a first cylindrical sheathing having a contact area that is exposed to the surrounding medium. The sheathing is in the form of a flexible hose or bellows through which the electrical connecting line of the plate is routed to the outside. The sensor should also be easy to position.

The use of two or more plates between which the conductivity or impedance of a medium surrounding the plates can be measured enables a straightforward, low-cost design of an electric sensor, which is therefore also suitable for use as a single-use sensor. By arranging at least one first plate on a closed, free end of a first cylindrical sheathing, the at least one plate can be positioned easily at an intended place within the container interior. By designing the sheathing as a flexible hose or bellows, an empty container can be folded up to a low volume, packed and sterilized. Within the scope of this application, "hose" should also be understood to mean a hose or bag-shaped film. The cross-section of the sheathing does not have to be circular and can be oval or rectangular in shape, for example. Use of a sheathing provides, on the one hand, the necessary flexibility and on the other hand, a straightforward connecting line to the exterior. At the same time, the necessary sealing and freedom from contamination vis-à-vis the environment are ensured.

A tube may be arranged within the cylindrical sheathing and may be longitudinally displaceable vis-à-vis a wall aperture. The tube may be designed as a bellows, and the end of said tube facing the plate may be connected to the free end of the bellows. In one embodiment, the end of the longitudinally displaceable tube facing away from the plate projects out of the container interior. Instead of the tube, a guide rod can also be used. The longitudinally displaceable tube enables, on the one hand, subsequent height adjustment of the at least one sensor plate and, on the other hand, the less flexible, longitudinally displaceable tube can be largely pulled out of the container interior to permit low-volume folding of the container. Use of a bellows additionally provides a reliable solution for the existing sealing and contamination problem between the wall aperture and the longitudinally displaceable tube. To the extent that the end of the longitudinally displaceable tube facing away from the plate projects out of the container interior, it is easier to displace the tube in a longitudinal direction. In principle, the rigid tube can also be designed to be telescopically extendable.

According to another embodiment, the wall aperture has an adapter piece in which the longitudinally displaceable tube is arranged and whose end facing the container interior is connected to the bellows.

The free end of the first sheathing may have a second plate arranged at a distance from the first plate. This arrangement ensures that the two plates necessary for conductivity or impedance measurement always have the same distance between them.

According to another embodiment, a second plate is arranged on the closed, free end of a second cylindrical sheathing with a contact surface exposed to a surrounding medium. This is especially advantageous when the two plates are to be arranged at different heights, or obliquely or transversely with respect to one another.

A second plate may be arranged directly on the inner side of the flexible wall facing the container interior and may have an exposed contact surface facing away from the wall. The second plate thus is fixed permanently fixed to the wall and therefore has a fixed position.

According to another embodiment, the contact surfaces of the plates are arranged above an intended fluid level. This allows for detection of foam present above the fluid level while also enabling detection of the rise in fluid level as it comes into contact with both plates.

Correspondingly, the sensor formed from at least two plates may be designed for detection of fluid and/or foam.

According to another embodiment, the control and regulating unit is connected to a pump or valve arranged in an inlet line between the flexible container and a reservoir containing an antifoam agent.

The container with the sensor may be a single-use container. In this case, the container, including sensor, is designed to be folded up and has the advantages already described above.

According to another embodiment, the container is used as a bioreactor.

Additional features and advantages of the invention are evident from the following specific description and the drawings.

DETAILED DESCRIPTION

Figure 1:
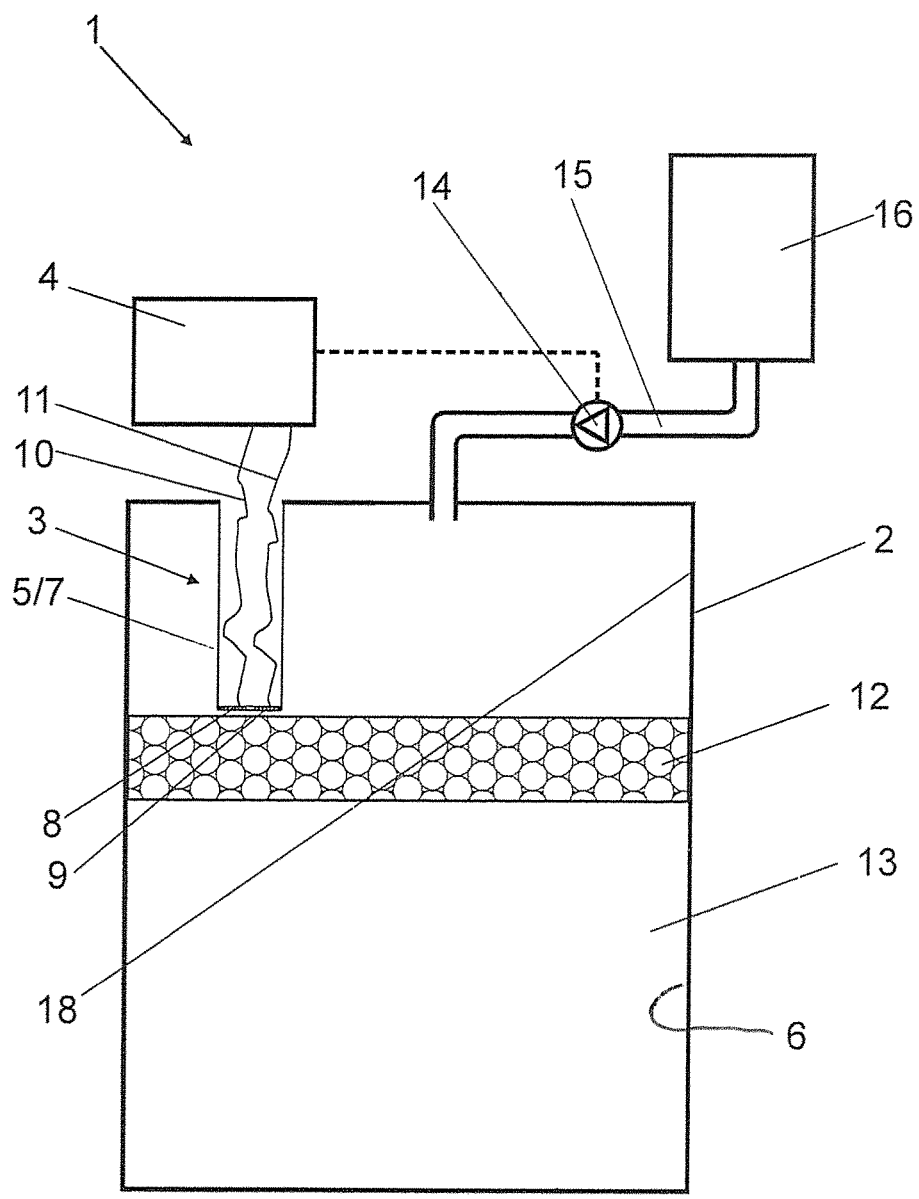
FIG. 1 is a schematic, lateral partial cross-sectional view of a bioreactor with a sensor that has two electrically conductive plates and, arranged on the exterior, a control and regulating unit, as well as an inlet line between a container containing an antifoam agent and the container of the bioreactor, as well as a pump arranged in the inlet line.

A container 2 with a flexible wall, for example of a bioreactor 1, essentially comprises a container interior 6, a sensor 3 and a control and regulating unit 4.

According to the exemplary embodiment of FIG. 1, the sensor 3 comprises a first cylindrical sheathing 5 that projects into the container interior 6 and is designed as a flexible hose 7. According to the exemplary embodiment of FIG. 1, at the free end of the first sheathing 5, which is cylindrically designed, there is arranged a first electrically conductive plate 8 and, at a distance, a second electrically conductive plate 9. The two plates 8, 9 are connected to the control and regulating unit 4 via connection lines 10, 11. By applying voltage, the conductivity or impedance of a medium in contact with the plates can be measured between the two plates 8, 9 by the control and regulating unit 4. In particular, it can be determined whether the two plates are in contact with gas, foam 12 or fluid 13. If desired a pump or valve 14 arranged in an inlet line 15 can be actuated via the control and regulating unit 4. In this case, the inlet line 15 connects a reservoir 16 that is filled with an antifoam agent to the container 2.

Figure 2:
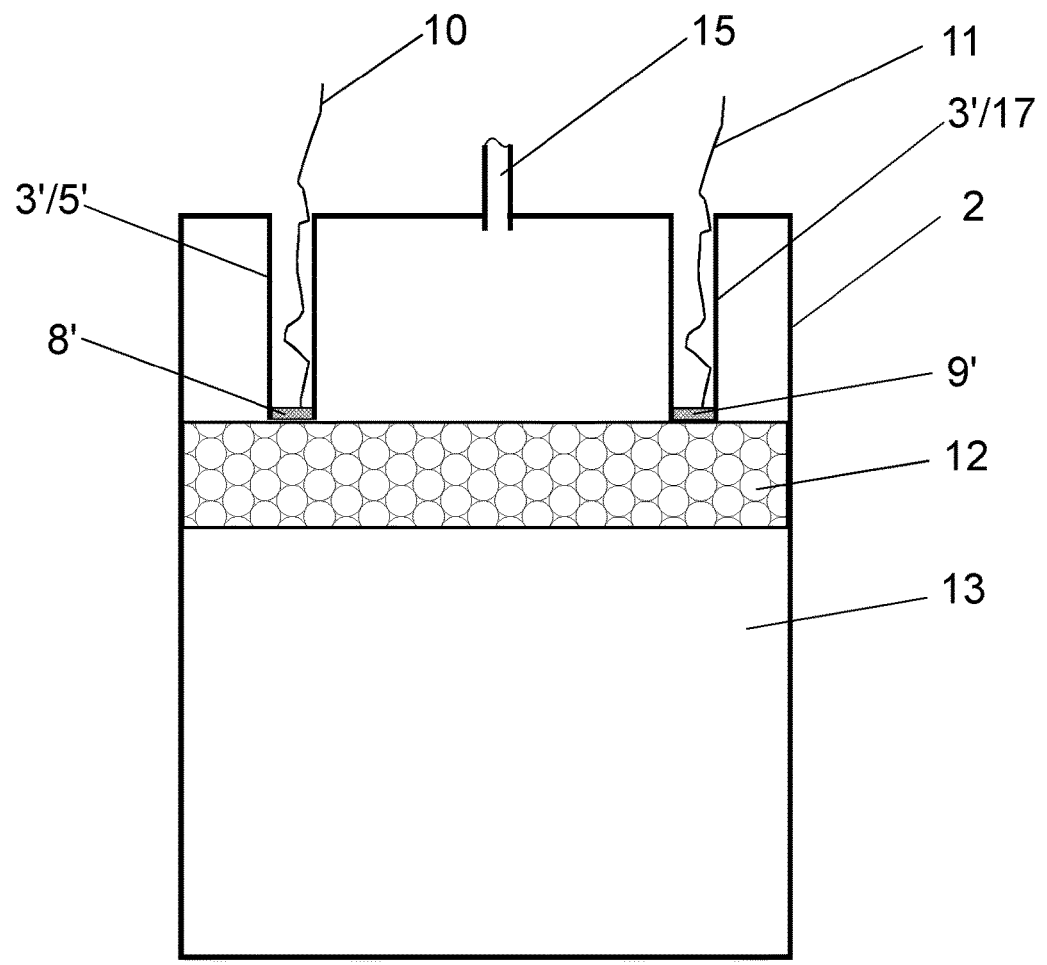
FIG. 2 shows a lateral view of another container with flexible walls and a sensor with two cylindrical sheathings, each with an electrically conductive plate.

According to the exemplary embodiment of FIG. 2, the sensor 3' comprises a first cylindrical sheathing 5' that has only a first plate 8' at its free end, and also a second cylindrical sheathing 17 that has a second plate 9' at its free end.

Figure 3:
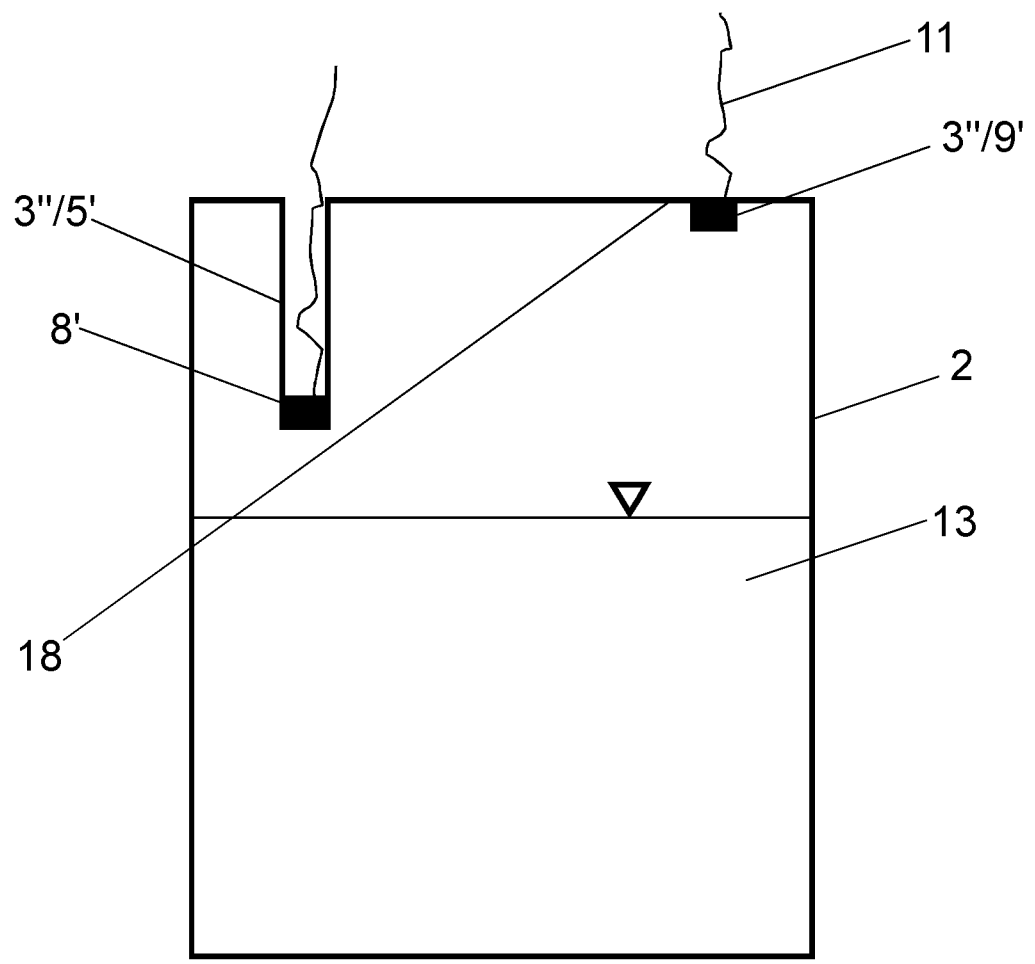
FIG. 3 shows a lateral partial cross-sectional view of another container with flexible walls with a sensor that has a cylindrical sheathing with a first plate, and having a second plate arranged on the flexible wall of the container.

According to the exemplary embodiment of FIG. 3, the sensor 3" comprises the first cylindrical sheathing 5' with the first plate 8', and also the second plate 9' that is arranged directly on the flexible wall 18 of the container 2.

Figure 4:
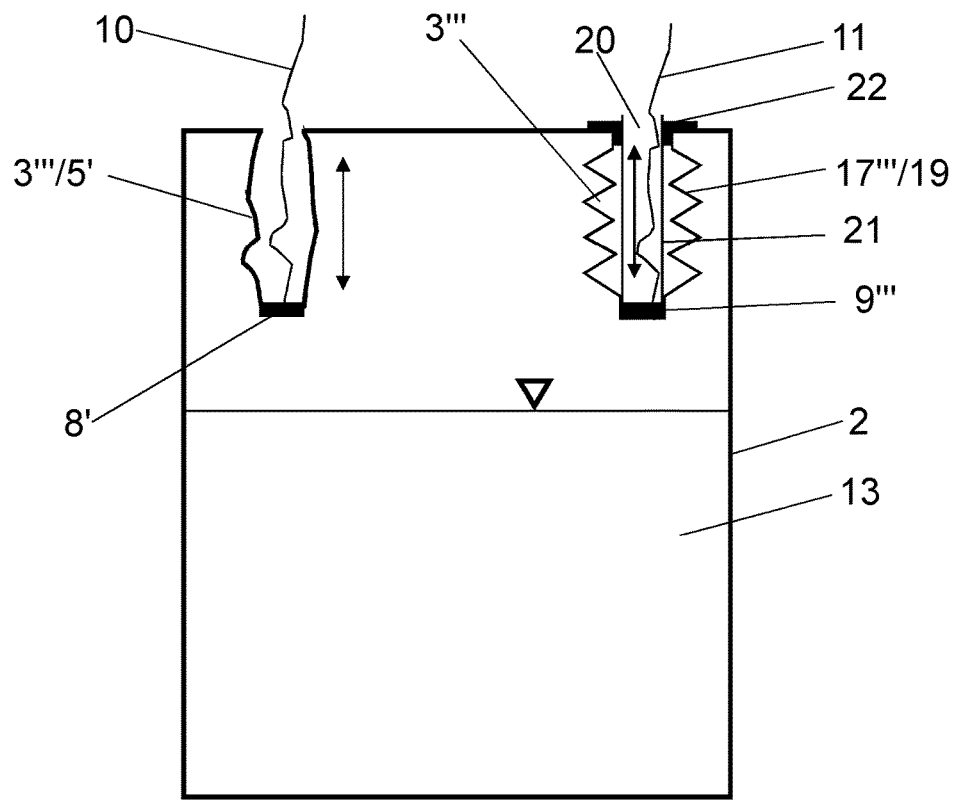
FIG. 4 shows a lateral cross-sectional view of another container with flexible walls and with a sensor that has a flexible sheathing with a first plate and a second cylindrical sheathing, designed as a bellows, in which a longitudinally displaceable tube is arranged, and which has a second plate at its free end.
Figure 5:
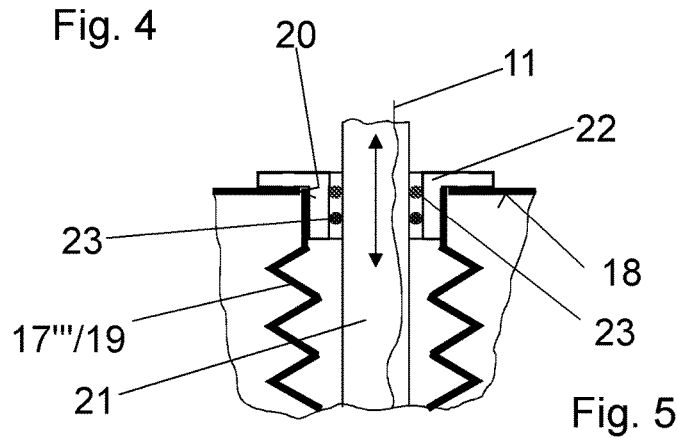
FIG. 5 shows a lateral cross-sectional detail view of the second cylindrical sheathing from FIG. 4, with adapter piece, bellows and displaceable tube.

According to the exemplary embodiment of FIG. 4, a sensor 3''' with a first sheathing 5' having a first plate 8', and a second sheathing 17''' designed as a bellows 19, at the end of which a second plate 9''' is arranged, is employed. A tube 21 that is longitudinally displaceable with respect to a wall aperture 20 is arranged within the cylindrical sheathing 17''', which is designed as a bellows 19, the end of said tube facing the plate 9''' being connected to the free end of the bellows 19 and/or to the plate 9'''. The wall aperture 20 has an adapter piece 22 in which the longitudinally displaceable tube 21 is arranged. The longitudinally displaceable tube 21 can be guided in the adapter piece 22 by means of sealing rings 23. FIG. 5 shows an enlarged detail view of the area of the adapter piece 22 of FIG. 4.

Figure 6:
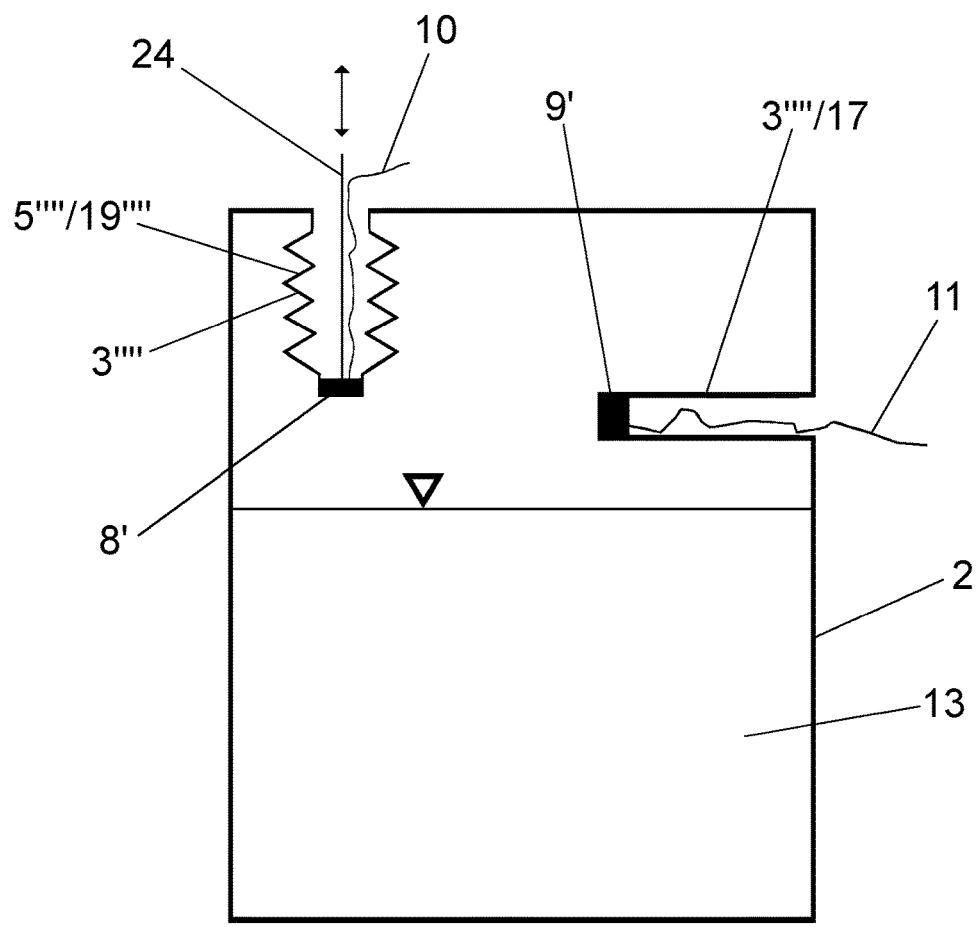
FIG. 6 shows a lateral cross-sectional view of another container with flexible walls, with a sensor that has a first cylindrical sheathing designed as a bellows, with a first plate on the free end of the bellows, and with a second cylindrical sheathing having a second plate, wherein the second cylindrical sheathing is arranged transversely with respect to the first cylindrical sheathing.

The exemplary embodiment of FIG. 6 shows a sensor 3'''' with a first sheathing 5'''' designed as a bellows 19'''', and a first plate 8'''' connected to a positioning rod 24. The first plate 8'''' can be adjusted to the desired measurement position or fill level using the positioning rod 24. Furthermore, the sensor 3"" has a second sheathing 17 arranged transversely with respect to the first sheathing 5'''.

Of course, the embodiments discussed in the specific description and shown in the figures are merely illustrative exemplary embodiments of the present invention. In light of this disclosure, a person skilled in the art is given a wide range of possible variations.

In particular, the individual sensors, the number of plates and their arrangement and combination can vary.

The invention claimed is:

1. A container (2) with flexible walls defining a container interior (6) and at least one wall aperture (20) formed in at least a first of the flexible walls, a first sheathing (5, 5', 5") having a first end connected to the first flexible wall so that an interior of the first sheathing (5, 5', 5"") communicates with the at least one wall aperture (20), the first sheathing (5, 5', 5"") having a closed free second end in the container interior (6), at least one electrical sensor (3, 3', 3", 3''', 3"") having at least first and second electrically conductive plates (8, 8', 9, 9', 9'''), each of which has a contact surface disposed to be exposed to a medium in the container (2), the electrically conductive plates (8, 8', 9, 9', 9''') being connected via connecting lines (10, 11) to an external area that is arranged outside the container interior (6), at least the first plate (8, 8') being arranged on the closed, free second end of a first sheathing (5, 5', 5""), and the electrical connecting line (10, 11) of at least the first plate (8, 8') being routed through the first sheathing (5, 5', 5") to the external area, wherein
the first sheathing (5, 5', 5"", 17, 17"") is a flexible hose (7) or folding bellows (19, 19"") that is adjustable in length in the container interior (6), so that at least the first plate (8, 8') is moveable with the closed, free second end of the first sheathing (5, 5', 5"") to plural positions relative to the medium in the container (2).

2. The container of claim 1, further comprising a tube (21) or a positioning rod (24) that is longitudinally displaceable with respect to the wall aperture (20), the tube (21) or the positioning rod (24) being arranged within the first sheathing (5"", 17""), which is designed as the bellows (19, 19""), an end of the tube or the rod facing toward the plate (8', 9''') being connected to the free second end of the bellows (19, 19"").

3. The container of claim 2, wherein the end of the longitudinally displaceable tube (21) that faces away from the plate (9''') projects outside of the container interior (6).

4. The container of claim 2, wherein the wall aperture (20) has an adapter piece (22) in which the longitudinally displaceable tube (21) is arranged, the end of the tube facing the container interior (6) being connected to the bellows (19).

5. The container of claim 1, wherein the free second end of the first sheathing (5) has a second plate (9) arranged at a distance from the first plate (8).

6. The container of claim 1, further comprising a second sheathing (17, 17''') with a closed free end, the second plate (9', 9''') being arranged on the closed, free end of the second sheathing (17, 17''').

7. The container of claim 1, wherein the second plate (9') is arranged directly on an inner side of the flexible wall (18) facing the container interior (6) and the exposed contact surface of the second plate (9') facing away from the wall (18).

8. The container of claim 1, wherein the contact surfaces of the plates (8, 8', 9, 9', 9''') are arranged above an intended fluid level.

9. The container of claim 1, wherein the sensor (3, 3', 3", 3''', 3"") formed by the at least first and second plates (8, 8', 9, 9', 9''') is designed for detection of fluid (13) and/or foam (12).

10. The container of claim 9, further comprising a pump or a valve (14) arranged in an inlet line (15) running between the flexible container (2) and a reservoir (16) containing an antifoam agent.

11. The container of claim 1, wherein the container (2) with the sensor (3, 3', 3", 3''', 3"") is a single-use container.

12. The container of claim 1, wherein the container (2) with the sensor (3, 3', 3", 3''', 3"") is designed so as to be capable of being folded up.

13. The container of claim 1, wherein the container (2) is a bioreactor (1).

* * * * *